US012642582B2

(12) United States Patent
Davies et al.

(10) Patent No.: US 12,642,582 B2
(45) Date of Patent: Jun. 2, 2026

(54) MEDICAL DILATOR, AND SYSTEMS, METHODS, AND KITS FOR MEDICAL DILATION

(71) Applicant: Boston Scientific Medical Device Limited, Ballybrit (IE)

(72) Inventors: Gareth Davies, Toronto (CA); John Paul Urbanski, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 1017 days.

(21) Appl. No.: 17/627,739

(22) PCT Filed: Jul. 17, 2020

(86) PCT No.: PCT/IB2020/056759
§ 371 (c)(1),
(2) Date: Jan. 17, 2022

(87) PCT Pub. No.: WO2021/014316
PCT Pub. Date: Jan. 28, 2021

(65) Prior Publication Data
US 2022/0257313 A1      Aug. 18, 2022

Related U.S. Application Data

(60) Provisional application No. 62/876,192, filed on Jul. 19, 2019.

(51) Int. Cl.
*A61B 18/14* (2006.01)
*A61B 5/367* (2021.01)
*A61B 17/00* (2006.01)

(52) U.S. Cl.
CPC .......... *A61B 18/1487* (2013.01); *A61B 5/367* (2021.01); *A61B 18/1492* (2013.01); *A61B 2017/00336* (2013.01)

(58) Field of Classification Search
CPC . A61B 18/1487; A61B 5/367; A61B 18/1492; A61B 2017/00336; A61B 34/20;
(Continued)

(56) References Cited

U.S. PATENT DOCUMENTS

| | | |
|---|---|---|
| 175,254 A | 3/1876 | Oberly |
| 827,626 A | 7/1906 | Gillet |

(Continued)

FOREIGN PATENT DOCUMENTS

| | | |
|---|---|---|
| CN | 107847260 A | 3/2018 |
| CN | 109481009 A | 3/2019 |

(Continued)

OTHER PUBLICATIONS

International Search Report and Written Opinion received for PCT Patent Application No. PCT/IB2020/056759, mailed on Oct. 22, 2020, 12 pages.

(Continued)

*Primary Examiner* — Theodore J Stigell
(74) *Attorney, Agent, or Firm* — Nelson Mullins Riley & Scarborough LLP

(57) ABSTRACT

A medical dilator includes an elongate member having a proximal end portion, an opposed distal end portion, and a lumen extending through the elongate member from the proximal end portion to the distal end portion. A dilating tip is at the distal end portion. The dilating tip has a first end of enlarged cross-sectional area and tapers going in the distal direction to a second end of reduced cross-sectional area. At least a first electrode is associated with the dilating tip. An electrical conductor is electrically connected to the first electrode and extends proximally from the first electrode towards the proximal end portion for electrical connection with an electro anatomical mapping system.

18 Claims, 9 Drawing Sheets

(58) Field of Classification Search
CPC ........... A61B 2017/00053; A61B 2018/00357;
A61B 2018/0038; A61B 2018/00601;
A61B 2018/00839; A61B 2034/2051;
A61B 2034/2072; A61B 2090/3925;
A61B 2090/3966; A61B 5/06; A61B
18/00; A61B 2018/00351; A61B
2018/00613; A61M 29/00
See application file for complete search history.

(56) References Cited

U.S. PATENT DOCUMENTS

| | | | |
|---|---|---|---|
| 848,711 A | 4/1907 | Weaver | |
| 1,072,954 A | 9/1913 | Junn | |
| 1,279,654 A | 9/1918 | Charlesworth | |
| 1,918,094 A | 7/1933 | Geekas | |
| 1,996,986 A | 4/1935 | Weinberg | |
| 2,021,989 A | 11/1935 | De Master | |
| 2,146,636 A | 2/1939 | Lipchow | |
| 3,429,574 A | 2/1969 | Williams | |
| 3,448,739 A | 6/1969 | Stark et al. | |
| 3,575,415 A | 4/1971 | Fulp et al. | |
| 3,595,239 A | 7/1971 | Petersen | |
| 3,995,623 A * | 12/1976 | Blake | A61B 5/287 |
| | | | 607/125 |
| 4,129,129 A | 12/1978 | Amrine | |
| 4,244,362 A | 1/1981 | Anderson | |
| 4,401,124 A | 8/1983 | Guess et al. | |
| 4,639,252 A | 1/1987 | Kelly et al. | |
| 4,641,649 A | 2/1987 | Walinsky et al. | |
| 4,669,467 A | 6/1987 | Willett et al. | |
| 4,682,596 A | 7/1987 | Bales et al. | |
| 4,790,311 A | 12/1988 | Ruiz | |
| 4,790,809 A | 12/1988 | Kuntz | |
| 4,793,350 A | 12/1988 | Mar et al. | |
| 4,807,620 A | 2/1989 | Strul et al. | |
| 4,832,048 A | 5/1989 | Cohen | |
| 4,840,622 A | 6/1989 | Hardy | |
| 4,863,441 A | 9/1989 | Lindsay et al. | |
| 4,884,567 A | 12/1989 | Elliott et al. | |
| 4,892,104 A | 1/1990 | Ito et al. | |
| 4,896,671 A | 1/1990 | Cunningham et al. | |
| 4,928,693 A | 5/1990 | Goodin et al. | |
| 4,936,281 A | 6/1990 | Stasz | |
| 4,960,410 A | 10/1990 | Pinchuk | |
| 4,977,897 A | 12/1990 | Hurwitz | |
| 4,998,933 A | 3/1991 | Eggers et al. | |
| 5,006,119 A | 4/1991 | Acker et al. | |
| 5,019,076 A | 5/1991 | Yamanashi et al. | |
| 5,047,026 A | 9/1991 | Rydell | |
| 5,081,997 A | 1/1992 | Bosley et al. | |
| 5,098,431 A | 3/1992 | Rydell | |
| 5,112,048 A | 5/1992 | Kienle | |
| 5,154,724 A | 10/1992 | Andrews | |
| 5,201,756 A | 4/1993 | Horzewski et al. | |
| 5,209,741 A | 5/1993 | Spaeth | |
| 5,211,183 A | 5/1993 | Wilson | |
| 5,221,256 A | 6/1993 | Mahurkar | |
| 5,230,349 A | 7/1993 | Langberg | |
| 5,281,216 A | 1/1994 | Klicek | |
| 5,300,068 A | 4/1994 | Rosar et al. | |
| 5,300,069 A | 4/1994 | Hunsberger et al. | |
| 5,314,418 A | 5/1994 | Takano et al. | |
| 5,318,525 A | 6/1994 | West et al. | |
| 5,327,905 A | 7/1994 | Avitall | |
| 5,364,393 A | 11/1994 | Auth et al. | |
| 5,372,596 A | 12/1994 | Klicek et al. | |
| 5,380,304 A | 1/1995 | Parker | |
| 5,397,304 A | 3/1995 | Truckai | |
| 5,403,338 A | 4/1995 | Milo | |
| 5,423,809 A | 6/1995 | Klicek | |
| 5,425,382 A | 6/1995 | Golden et al. | |
| 5,490,859 A | 2/1996 | Mische et al. | |
| 5,497,774 A | 3/1996 | Swartz et al. | |
| 5,507,751 A | 4/1996 | Goode et al. | |
| 5,509,411 A | 4/1996 | Littmann et al. | |
| 5,540,681 A | 7/1996 | Strul et al. | |
| 5,545,200 A | 8/1996 | West et al. | |
| 5,555,618 A | 9/1996 | Winkler | |
| 5,571,088 A | 11/1996 | Lennox et al. | |
| 5,575,766 A | 11/1996 | Swartz et al. | |
| 5,575,772 A | 11/1996 | Lennox | |
| 5,599,347 A | 2/1997 | Hart et al. | |
| 5,605,162 A | 2/1997 | Mirzaee et al. | |
| 5,617,878 A | 4/1997 | Taheri | |
| 5,622,169 A | 4/1997 | Golden et al. | |
| 5,624,430 A | 4/1997 | Eton et al. | |
| 5,667,488 A | 9/1997 | Lundquist et al. | |
| 5,673,695 A | 10/1997 | Mcgee et al. | |
| 5,674,208 A | 10/1997 | Berg et al. | |
| 5,683,366 A | 11/1997 | Eggers et al. | |
| 5,720,744 A | 2/1998 | Eggleston et al. | |
| 5,741,249 A | 4/1998 | Moss et al. | |
| 5,766,135 A | 6/1998 | Terwilliger | |
| 5,779,688 A | 7/1998 | Imran et al. | |
| 5,810,764 A | 9/1998 | Eggers et al. | |
| 5,814,028 A | 9/1998 | Swartz et al. | |
| 5,830,214 A | 11/1998 | Flom et al. | |
| 5,836,875 A | 11/1998 | Webster, Jr. | |
| 5,849,011 A | 12/1998 | Jones et al. | |
| 5,851,210 A | 12/1998 | Torossian | |
| 5,885,227 A | 3/1999 | Finlayson | |
| 5,888,201 A | 3/1999 | Stinson et al. | |
| 5,893,848 A | 4/1999 | Negus et al. | |
| 5,893,885 A | 4/1999 | Webster, Jr. | |
| 5,904,679 A | 5/1999 | Clayman | |
| 5,916,210 A | 6/1999 | Winston | |
| 5,921,957 A | 7/1999 | Killion et al. | |
| 5,931,818 A | 8/1999 | Werp et al. | |
| 5,944,023 A | 8/1999 | Johnson et al. | |
| 5,951,482 A | 9/1999 | Winston et al. | |
| 5,957,842 A | 9/1999 | Littmann et al. | |
| 5,964,757 A | 10/1999 | Ponzi | |
| 5,967,976 A | 10/1999 | Larsen et al. | |
| 5,989,276 A | 11/1999 | Houser et al. | |
| 6,007,555 A | 12/1999 | Devine | |
| 6,009,877 A | 1/2000 | Edwards | |
| 6,013,072 A | 1/2000 | Winston et al. | |
| 6,017,340 A | 1/2000 | Cassidy et al. | |
| 6,018,676 A | 1/2000 | Davis et al. | |
| 6,030,380 A | 2/2000 | Auth et al. | |
| 6,032,674 A | 3/2000 | Eggers et al. | |
| 6,048,349 A | 4/2000 | Winston et al. | |
| 6,053,870 A | 4/2000 | Fulton, III | |
| 6,053,904 A | 4/2000 | Scribner et al. | |
| 6,056,747 A | 5/2000 | Saadat et al. | |
| 6,063,093 A | 5/2000 | Winston et al. | |
| 6,093,185 A | 7/2000 | Ellis et al. | |
| 6,106,515 A | 8/2000 | Winston et al. | |
| 6,106,520 A | 8/2000 | Laufer et al. | |
| 6,117,131 A | 9/2000 | Taylor | |
| 6,142,992 A | 11/2000 | Cheng et al. | |
| 6,146,380 A | 11/2000 | Racz et al. | |
| 6,155,264 A | 12/2000 | Ressemann et al. | |
| 6,156,031 A | 12/2000 | Aita et al. | |
| 6,171,305 B1 | 1/2001 | Sherman | |
| 6,179,824 B1 | 1/2001 | Eggers et al. | |
| 6,193,676 B1 | 2/2001 | Winston et al. | |
| 6,193,715 B1 | 2/2001 | Wrublewski et al. | |
| 6,210,408 B1 | 4/2001 | Chandrasekaran et al. | |
| 6,217,575 B1 | 4/2001 | Devore et al. | |
| 6,221,061 B1 | 4/2001 | Engelson et al. | |
| 6,228,076 B1 | 5/2001 | Winston et al. | |
| 6,245,054 B1 | 6/2001 | Fuimaono et al. | |
| 6,267,758 B1 | 7/2001 | Daw et al. | |
| 6,283,983 B1 | 9/2001 | Makower et al. | |
| 6,292,678 B1 | 9/2001 | Hall et al. | |
| 6,293,945 B1 | 9/2001 | Parins et al. | |
| 6,296,615 B1 | 10/2001 | Brockway et al. | |
| 6,296,636 B1 | 10/2001 | Cheng et al. | |
| 6,302,898 B1 | 10/2001 | Edwards et al. | |
| 6,304,769 B1 | 10/2001 | Arenson et al. | |
| 6,315,777 B1 | 11/2001 | Comben | |
| 6,328,699 B1 | 12/2001 | Eigler et al. | |

(56) References Cited

U.S. PATENT DOCUMENTS

| | | | |
|---|---|---|---|
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Esh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2001/0051790 A1* | 12/2001 | Parker ............... A61M 25/005 |
| | | | 604/524 |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | Mcguckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | Mcmichael et al. |
| 2004/0015162 A1 | 1/2004 | Mcgaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Molante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | Mcclurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0089691 A1* | 4/2006 | Kaplan ................. A61N 1/056 |
| | | | 607/116 |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |

(56)        References Cited

U.S. PATENT DOCUMENTS

| | | |
|---|---|---|
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2010/0318081 A1 | 12/2010 | Sato et al. |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2011/0224666 A1 | 9/2011 | Davies et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0096455 A1* | 4/2013 | Kassab .................. H01B 7/048 |
| | | 174/113 C |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2017/0079541 A1 | 3/2017 | Krishnan |
| 2018/0161085 A1 | 6/2018 | Shin et al. |
| 2018/0169383 A1* | 6/2018 | Khalaj .................. A61B 8/481 |
| 2019/0021763 A1 | 1/2019 | Zhou et al. |
| 2019/0247035 A1 | 8/2019 | Gittard et al. |

FOREIGN PATENT DOCUMENTS

| | | |
|---|---|---|
| JP | 2002-532164 A | 10/2002 |
| JP | 4674969 B2 | 4/2011 |
| JP | 2017-512569 A | 5/2017 |
| JP | 2018-525055 A | 9/2018 |
| WO | 00/35527 A2 | 6/2000 |
| WO | WO-2018/165277 A1 * | 9/2018 |

OTHER PUBLICATIONS

Notice of Reasons for Refusal received for Japanese Patent Application No. 2021-578182, mailed on May 7, 2024, 14 pages (7 pages of English Translation and 7 pages of Original Document).

CN Office Action, Including Search report received for Chinese Patent Application No. 202080045605.6, mailed on Feb. 22, 2025, 22 pages (10 pages of English Translation and 12 pages of Original Document).

Notice of Reasons for Refusal received for Japanese Patent Application No. 2024-228401, mailed on Feb. 3, 2026, 6 pages (3 pages of English Translation and 3 pages of Original Document).

* cited by examiner

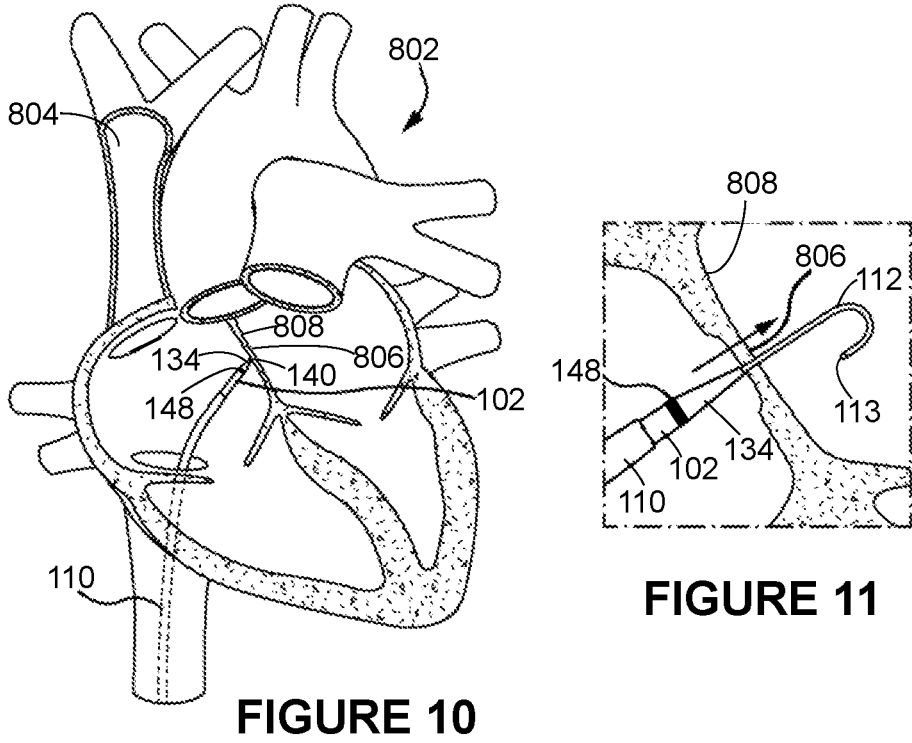
FIGURE 10
FIGURE 11
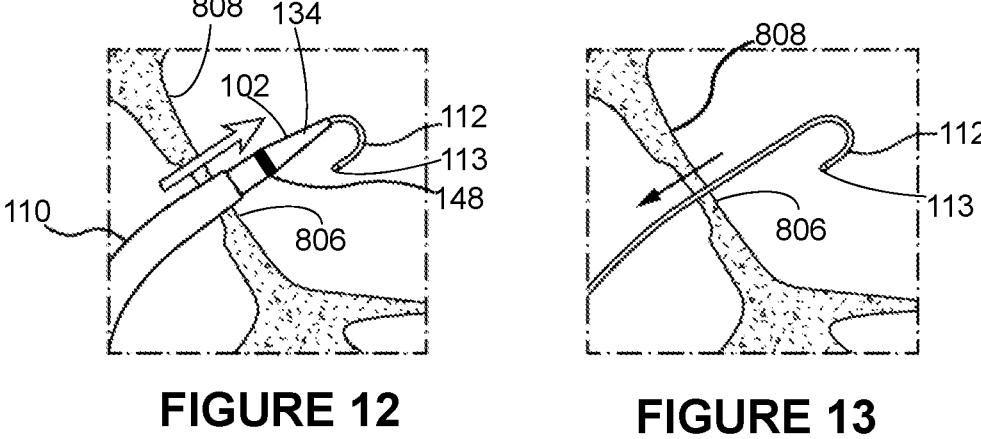
FIGURE 12
FIGURE 13

MEDICAL DILATOR, AND SYSTEMS, METHODS, AND KITS FOR MEDICAL DILATION

FIELD

This document relates to medical dilation, for example dilation of a surgically created perforation in cardiac tissue. More specifically, this document relates to a medical dilator, and related systems, methods, and kits.

SUMMARY

The following summary is intended to introduce the reader to various aspects of the detailed description, but not to define or delimit any invention.

According to some aspects, a medical dilator includes an elongate member having a proximal end portion, an opposed distal end portion, and a lumen extending through the elongate member from the proximal end portion to the distal end portion. A dilating tip is at the distal end portion. The dilating tip has a first end of enlarged cross-sectional area and tapers going in the distal direction to a second end of reduced cross-sectional area. At least a first electrode is associated with the dilating tip. An electrical conductor is electrically connected to the first electrode and extends proximally from the first electrode towards the proximal end portion for electrical connection with an electroanatomical mapping system.

In some examples, the first electrode is positioned between the first end of the dilating tip and the second end of the dilating tip. In some examples, the first electrode is positioned proximal of the first end of the dilating tip.

In some examples, the dilating tip has a tip circumferential outer surface having a circumferential groove defined therein, and the electrode is annular and is seated in the groove.

In some examples, the dilating tip has a tip circumferential outer surface, a tip circumferential inner surface, and a tip sidewall extending between the tip circumferential inner surface and the tip circumferential outer surface, and the electrical conductor extends from the electrode through the tip sidewall and into the lumen.

In some examples, the elongate member has a circumferential outer surface, a circumferential inner surface, and a sidewall extending along the length of the elongate member between the circumferential inner surface and the circumferential outer surface, and the electrical conductor is embedded in the sidewall and extends from the electrode to the proximal end portion. The circumferential outer surface can have a longitudinal groove defined therein and extending from the first electrode to the proximal end portion, and the electrical conductor can be seated in the longitudinal groove. Alternatively, the elongate member can include an outer tube defining the circumferential outer surface, and an inner liner within the outer tube and defining the circumferential inner surface, and the electrical conductor can be positioned between the outer tube and the inner liner. The electrical conductor can be a tubular braid.

In some examples, the first electrode is removable from the elongate member.

In some examples, the medical dilator further includes a second electrode mounted to the elongate member and spaced from the first electrode.

In some examples, the dilating tip includes a proximal piece having a distal-facing shoulder surface and a neck extending distally from the shoulder surface, the electrode is annular and is received on the neck and abuts the shoulder surface, and the dilating tip further includes a distal piece received on the neck distally of and abutting the electrode.

In some examples, the electrode is radiopaque. In some examples, the electrode includes platinum-iridium.

In some examples, the electrode has an echogenic profile. In some examples the electrode includes a coil.

According to some aspects, a kit of parts for medical perforation system includes a medical dilator, a sheath, and a perforation device. The medical dilator has an elongate member having a proximal end portion, an opposed distal end portion, and a lumen extending through the elongate member from the proximal end portion to the distal end portion. The medical dilator further has a dilating tip at the distal end portion, and the dilating tip has first end of enlarged cross-sectional area and tapers going in the distal direction to a second end of reduced cross-sectional area. The medical dilator further has at least a first electrode associated with the dilating tip, and an electrical conductor electrically connected to the first electrode and extending proximally from the first electrode to the proximal end portion for electrical connection with an electroanatomical mapping system. The sheath is for receiving the medical dilator. The perforation device is receivable in the lumen.

In some examples, the kit of parts further includes at least a second electrode. The second electrode can be secured to the sheath, or secured to the elongate member, or secured to the perforation device.

According to some aspects, a medical dilation system includes a medical dilator and an electroanatomical mapping system. The medical dilator includes an elongate member having a proximal end portion, an opposed distal end portion, and a lumen extending through the elongate member from the proximal end portion to the distal end portion. A dilating tip is at the distal end portion. The dilating tip has a first end of enlarged cross-sectional area, and tapers going in the distal direction to a second end of reduced cross-sectional area. At least a first electrode is associated with the dilating tip, and an electrical conductor is electrically connected to the first electrode and extends proximally from the first electrode to the proximal end portion. The electroanatomical mapping system is electrically connectable to the electrical conductor and is configured to receive an electroanatomical mapping signal from the electrode and determine a location of the dilating tip based on the electroanatomical mapping signal.

According to some aspects, a method for medical dilation includes a. advancing a dilating tip of a medical dilator towards a first target anatomical location; b. receiving a first electroanatomical mapping signal from an electrode associated with the dilating tip; and c. based on the first electroanatomical mapping signal, determining a first location of the dilating tip with respect to the first target anatomical location.

In some examples, after step c., the method further includes: d. advancing a perforation device out of the medical dilator, and creating a perforation in the first target anatomical location using the perforation device.

In some examples, the method further includes determining a location of the perforation device with respect to the dilating tip.

In some examples, after step d., the method further includes: e. advancing the electrode and the dilating tip through the perforation, to dilate the perforation.

In some examples, after or during step e., the method further includes: f. receiving a second electroanatomical mapping signal from the electrode, and g. based on the second electroanatomical mapping signal, determining a second location of the dilating tip with respect to the first target anatomical location. In some examples, the first target anatomical location is an atrial septum.

In some examples, the method further includes determining a location of the dilating tip with respect to a left atrial wall.

In some examples, step a. includes positioning the dilator within a sheath and advancing the dilator and the sheath towards the first target anatomical location, and the method further includes determining a location of the dilating tip with respect to a tip of the sheath.

BRIEF DESCRIPTION OF THE DRAWINGS

The accompanying drawings are for illustrating examples of articles, methods, and apparatuses of the present disclosure and are not intended to be limiting. In the drawings:

FIG. 10 is a schematic view showing a third step of the example method for creation and dilation of a transseptal perforation of FIG. 8;

FIG. 11 is a schematic view showing a fourth step of the example method for creation and dilation of a transseptal perforation of FIG. 8;

FIG. 12 is a schematic view showing a fifth step of the example method for creation and dilation of a transseptal perforation of FIG. 8; and FIG. 13 is a schematic view showing a second step of the example method for creation and dilation of a transseptal perforation of FIG. 8.

DETAILED DESCRIPTION

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein are medical dilators (also referred to herein simply as "dilators") that can be used for dilation of anatomical apertures, such as surgical perforations. For example, the dilators can be used in transseptal perforation procedures, in which a perforation is created in the atrial septum of the heart, optionally using a radiofrequency perforation device, and then dilated using a dilator. Such procedures can be carried out, for example, to gain access to the left atrium for a medical treatment.

In general, the dilators disclosed herein are configured to allow for non-fluoroscopic visualization and determination of the location of the tip of the dilator (also referred to herein as the "dilating tip") within the body, or of the location of the tip of the dilator with respect to other surgical tools (e.g. with respect to the perforation device or with respect to a sheath in which the dilator is housed). More specifically, the dilators disclosed herein can include at least one electrode associated with the tip thereof. The electrode can be an electroanatomical mapping (EAM) electrode. The EAM electrode can be connected to an EAM system, which can communicate EAM signals to and from the EAM electrode (either directly or via a pad), and based on the EAM signals received from the EAM electrode, can determine a location of the EAM electrode, and thus the tip of the dilator, within the body or with respect to other surgical tools. This can, for example, visualize the dilator tip to allow a user to determine whether the tip is positioned properly with respect to a target tissue, allow a user to confirm that the perforation device is shrouded within the dilator prior to perforation, and/or allow for a user to confirm that the dilating tip is sufficiently spaced from non-target tissues.

Figure 1:
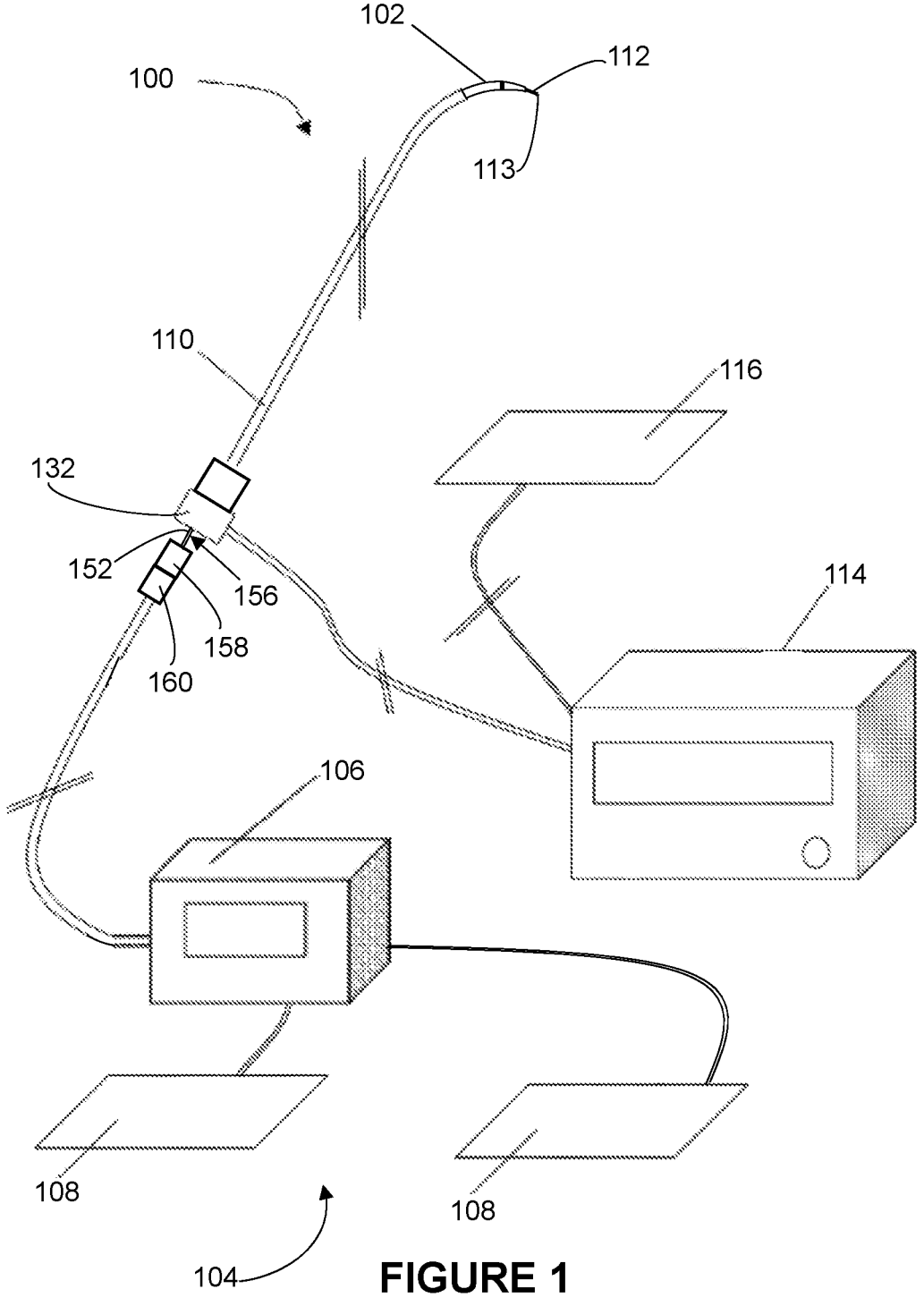
FIG. 1 is a perspective view of an example surgical perforation system.

Referring now to FIG. 1, an example surgical perforation system 100 is shown. The surgical perforation system 100 includes a dilator 102, an EAM system 104 including an EAM signal generator 106 and a set (e.g. 3 or more) of EAM pads 108 (only two of which are shown in FIG. 1), a sheath 110, a radiofrequency (RF) perforation device 112 having a perforation electrode 113 at its distal tip, and an RF generator 114 and grounding pad 116. The sheath 110, RF perforation device 112, RF generator 114, and grounding pad 116 will not be described in detail herein, and can optionally be those sold by Baylis Medical Company, Inc. (Montreal, Canada), for example under the brand names NRG® Transseptal Platform, or SupraCross® Transseptal Platform. Furthermore, in alternative examples, another type of perforation device, such as a mechanical perforation device, can be used instead of an RF perforation device. Optionally, some or all of the parts of the surgical perforation system 100 can be sold or provided together in a kit, either in an assembled state or in an unassembled state.

Figure 2:
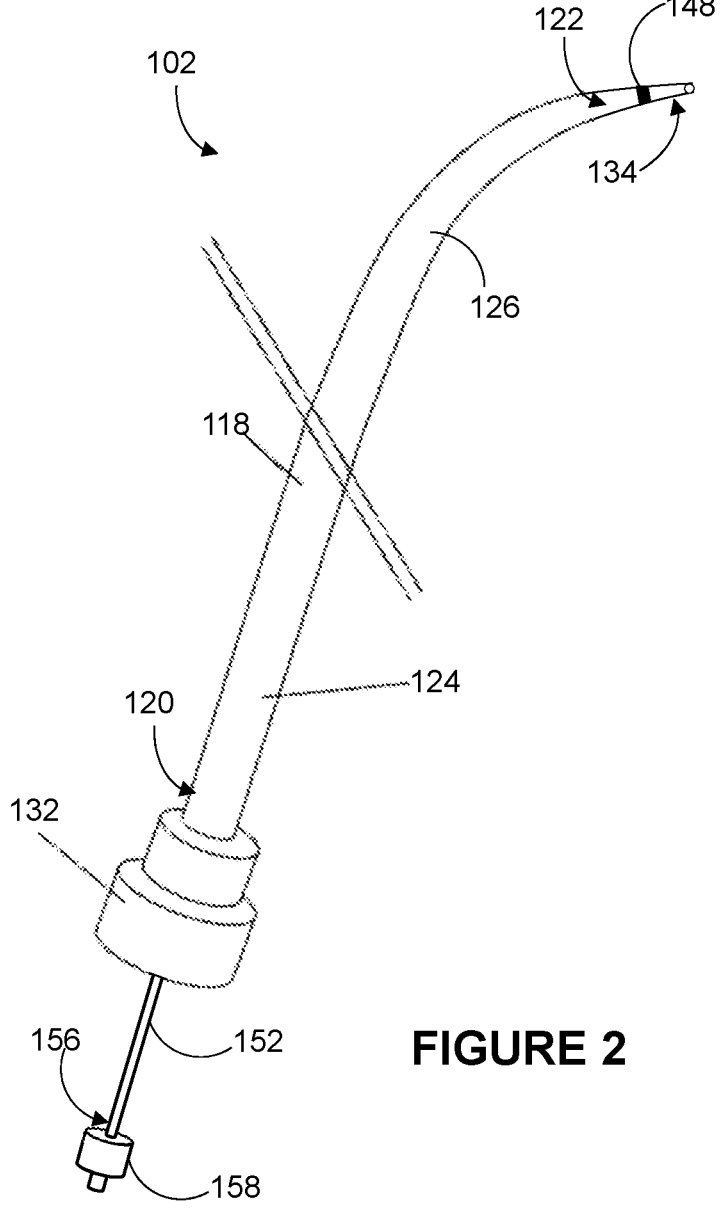
FIG. 2 is a perspective view of the dilator of the surgical perforation system of FIG. 1.

Referring now to FIG. 2, the dilator 102 is shown in greater detail. In the example shown, the dilator 102 includes an elongate member 118 having a proximal end portion 120, which in use is generally directed towards a user such as a surgeon, and an opposed distal end portion 122, which in use is generally directed towards a target location in a patient. The elongate member 118 includes a sidewall 124, which extends longitudinally between the proximal end portion 120 and the distal end portion 122, and radially between a circumferential outer surface 126 and a circumferential inner surface 128 (shown in FIGS. 3B and 3C). The circumferential inner surface 128 defines a lumen 130 (shown in FIGS. 3B and 3C), which extends through the elongate member 118 from the proximal end portion 120 to the distal end portion 122. In use, the lumen 130 can receive the RF perforation device 112.

The elongate member can be made from various materials, including but not limited to plastics such as high-density polyethylene (HDPE).

Referring still to FIG. 2, in the example shown, a handle 132 is mounted to the proximal end portion 120. The handle 132 can include various hubs and/or ports and/or connection points (not shown) for connection to various external devices.

Referring still to FIG. 2, the dilator 102 includes a dilating tip 134 at the distal end portion 122. The dilating tip 134 is shown in greater detail in FIGS. 3A to 3C. In the example shown, the dilating tip 134 includes a first end 136 and a second end 138 that is spaced distally from the first end 136. The dilating tip 134 tapers in cross-sectional area going from the first end 136 to the second end 138, so that the first end 136 has an enlarged cross-sectional area with respect to the second end 138, and the second end 138 has a reduced cross-sectional area with respect to the first end 136. As the dilating tip 134 is passed through an aperture, the enlargement in cross-sectional area dilates the aperture.

In the example shown, the second end 138 of the dilating tip 134 forms a distal end 140 of the dilator 102. In alternative examples (not shown), the dilating tip can be spaced proximally from the distal end of the dilator.

Figures 3A, 3B, 3C:
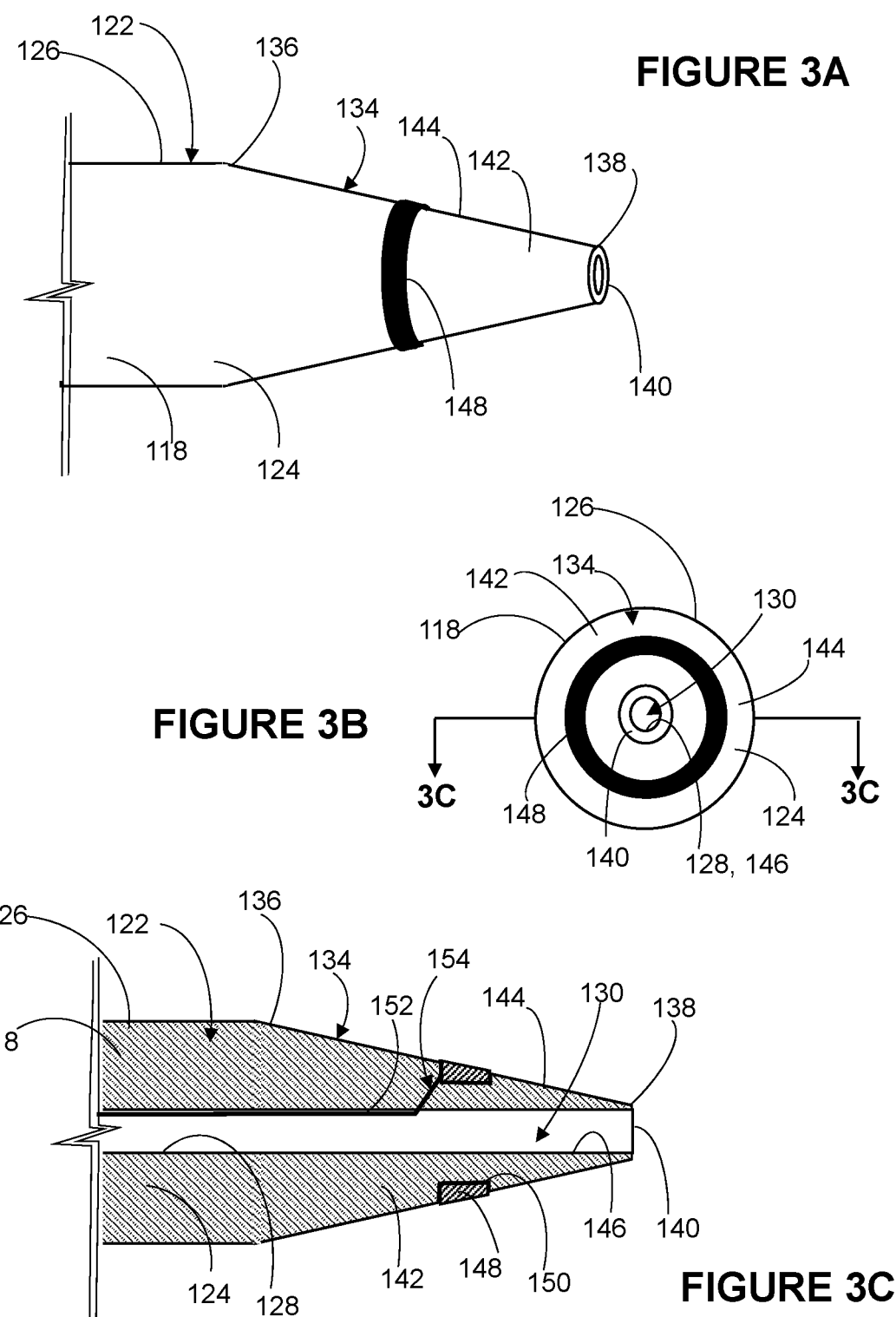
FIG. 3A is an enlarged view of the dilating tip of the dilator of FIG. 2.
FIG. 3B is an end view of the dilating tip of FIG. 3A.
FIG. 3C is a cross-section taken along line 3C-3C in FIG. 3B.

Referring still to FIGS. 3A to 3C, in the example shown, the dilating tip 134 has a sidewall 142 (also referred to herein as a "tip sidewall"), which extends longitudinally between the first end 136 of the dilating tip 134 and the second end 138 of the dilating tip 134, and radially between an circumferential outer surface 144 of the dilating tip 134 (also referred to herein as a 'tip circumferential outer surface") and an circumferential inner surface 146 of the dilating tip 134 (also referred to herein as a 'tip circumferential inner surface'). The tip sidewall 142, tip circumferential outer surface 144, and tip circumferential inner surface 146 form a part of the sidewall 124 of the elongate member 118, the circumferential outer surface 126 of the elongate member 118, and circumferential inner surface 128 of the elongate member 118, respectively.

Referring still to FIGS. 3A to 3C, the dilator further includes an EAM electrode 148, which is associated with the dilating tip 134. As described above, the EAM electrode 148 can allow for the location of the dilating tip 134 to be determined, for example the location of the dilating tip 134 within the body, or the location of the dilating tip 134 with respect to other parts of the surgical perforation system 100. The EAM electrode 148 can be, for example, annular, and can be made of or can include stainless steel or platinum-iridium. In some examples, the EAM electrode can additionally be radiopaque, which can allow for visualization of the electrode using fluoroscopy, if desired. In further examples, the EAM electrode can have an echogenic profile, which can allow for visualization of the electrode using ultrasound, if desired. For example, the EAM electrode can include a coil. In some examples, the EAM electrode 148 can be made of a conductive paint.

As mentioned above, the EAM electrode 148 is associated with the dilating tip 134. The term "associated with" indicates that the EAM electrode 148 is positioned to allow for the determination of the location of the dilating tip 134, whether directly (e.g. in cases where the EAM electrode 148 is mounted directly to the dilating tip 134), or indirectly (e.g. in cases where the EAM electrode 148 is spaced from the dilating tip 134 and where an extrapolation is carried out to determine the location of the dilating tip 134 based on the location of the EAM electrode 148).

In the example shown, the EAM electrode 148 is annular and extends circumferentially around the dilating tip 134, and is positioned between the first end 136 of the dilating tip 134 and the second end 138 of the dilating tip 134. In alternative examples (e.g. as shown in FIGS. 5A to 5D), the EAM electrode can be positioned proximal of the dilating tip, or distal of the dilating tip. In such examples, as mentioned above, an extrapolation can be carried out to determine the location of the dilating tip based on the location of the EAM electrode.

Referring to FIG. 3C, in the example shown, the circumferential outer surface 144 of the dilating tip 134 has a circumferential groove 150 defined therein, and the EAM electrode 148 is seated in the groove 150. The EAM electrode 148 can be secured in the groove 150 in a variety of ways, such as by gluing, welding, soldering, and/or by friction. Furthermore, in the example shown, the EAM electrode 148 is profiled to match the taper of the dilating tip 134, so that the outer surface of the EAM electrode 148 is flush with the circumferential outer surface 144 of the dilating tip 134. This can be achieved, for example, by swaging. This can allow for a smooth transition as the dilating tip 134 is passed through an aperture.

In the example shown, the dilating tip 134 is of a one-piece construction. In alternative examples, as will be described below with reference to FIGS. 4A to 4C, the dilating tip can be of a multi-piece construction.

Referring still to FIGS. 3A to 3C, an electrical conductor 152 is connected to the EAM electrode 148, and extends proximally from the EAM electrode 148 towards the proximal end portion 120 (not shown in FIGS. 3A to 3C) of the elongate member 118, for connection to the EAM signal generator 106 of the EAM system 104 (not shown in FIGS. 3A to 3C). The electrical conductor 152 is electrically insulated between the EAM electrode 148 and its connection to the EAM signal generator 106, so that electrical signals can be communicated between the EAM electrode 148 and the EAM system 104. For example, the electrical conductor 152 can include a layer of polyimide insulation.

The end of the electrical conductor 152 that is connected to the EAM electrode 148 may be referred to herein as the 'electrode end portion 154' of the electrical conductor 152 (shown in FIG. 3C), and the end of the electrical conductor 152 that is connectable to the EAM system 104 may be referred to herein as the 'system end portion 156' of the electrical conductor 152 (shown in FIGS. 1 and 2). The system end portion 156 of the electrical conductor 152 may be connected or connectable to the EAM signal generator 106 in various ways. In the example shown, a connector 158 is mounted to the system end portion 156. The connector 158 is mateable with a connector 160 of the EAM signal generator 106. Alternatively, clips (e.g. alligator clips) may be used to connect the system end portion of the electrical conductor to the EAM system (not shown).

Referring still to FIGS. 3A to 3C, in the example shown, the electrical conductor 152 extends from the EAM electrode 148, through the tip sidewall 142, and into the lumen 130. The electrical conductor 152 then extends through the lumen 130 to the proximal end portion 120 of the elongate member 118. In alternative examples, as will be described below, the electrical conductor can be embedded within the sidewall of the elongate member.

As mentioned above, in the example shown, the EAM system 104 includes the EAM signal generator 106 and a pair of EAM pads 108. Such systems are commercially available, for example under the brand names ENSITE PRECISION™ and CARTO®, and are not described in detail herein. Briefly, by routing electrical signals from the EAM signal generator 106 to the EAM pads 108, from the EAM pads 108 to the EAM electrode 148, and from the EAM electrode 148 back to the EAM signal generator 106 (or in the reverse order—i.e. from the EAM signal generator 106 to the EAM electrode 148, from the EAM electrode 148 to the EAM pads 108, and from the EAM pads 108 back to the EAM signal generator 106), the EAM electrode 148 may be visualized, and thus the location of the dilating tip 134, can be determined.

In the example shown, the perforation electrode 113 of the RF perforation device 112 can also be used as an additional EAM electrode. That is, together with the EAM electrode 148 of the dilator 102, the perforation electrode 113 of the RF perforation device 112 can be electrically connected to the EAM system 104, so that its location can be determined by the EAM system 104.

Figures 4A, 4B, 4C:
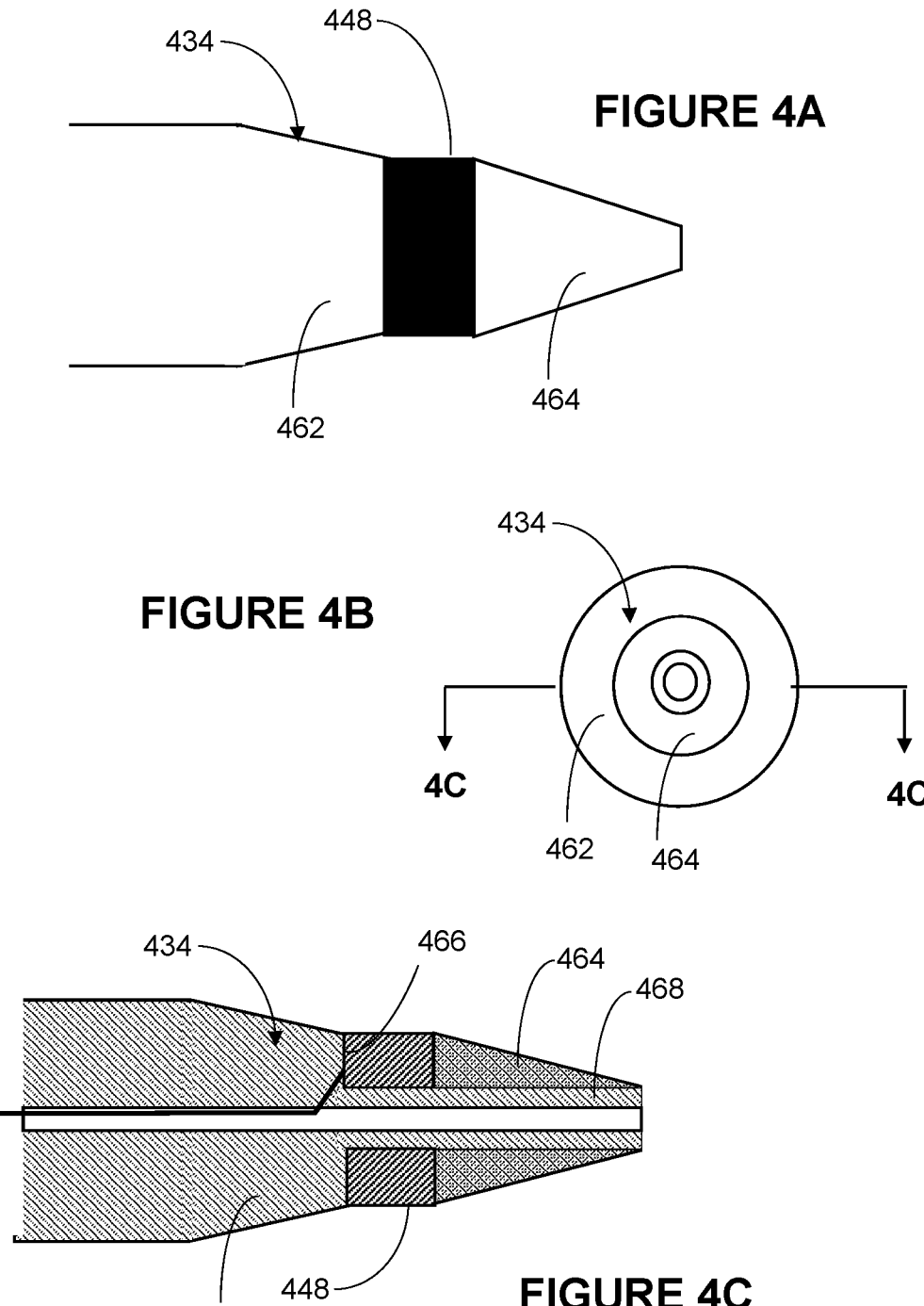
FIG. 4A is an enlarged view of another example dilating tip.
FIG. 4B is an end view of the dilating tip of FIG. 4A.
FIG. 4C is a cross-section taken along line 4C-4C in FIG. 4B.
Figures 5A, 5B, 5C, 5D:
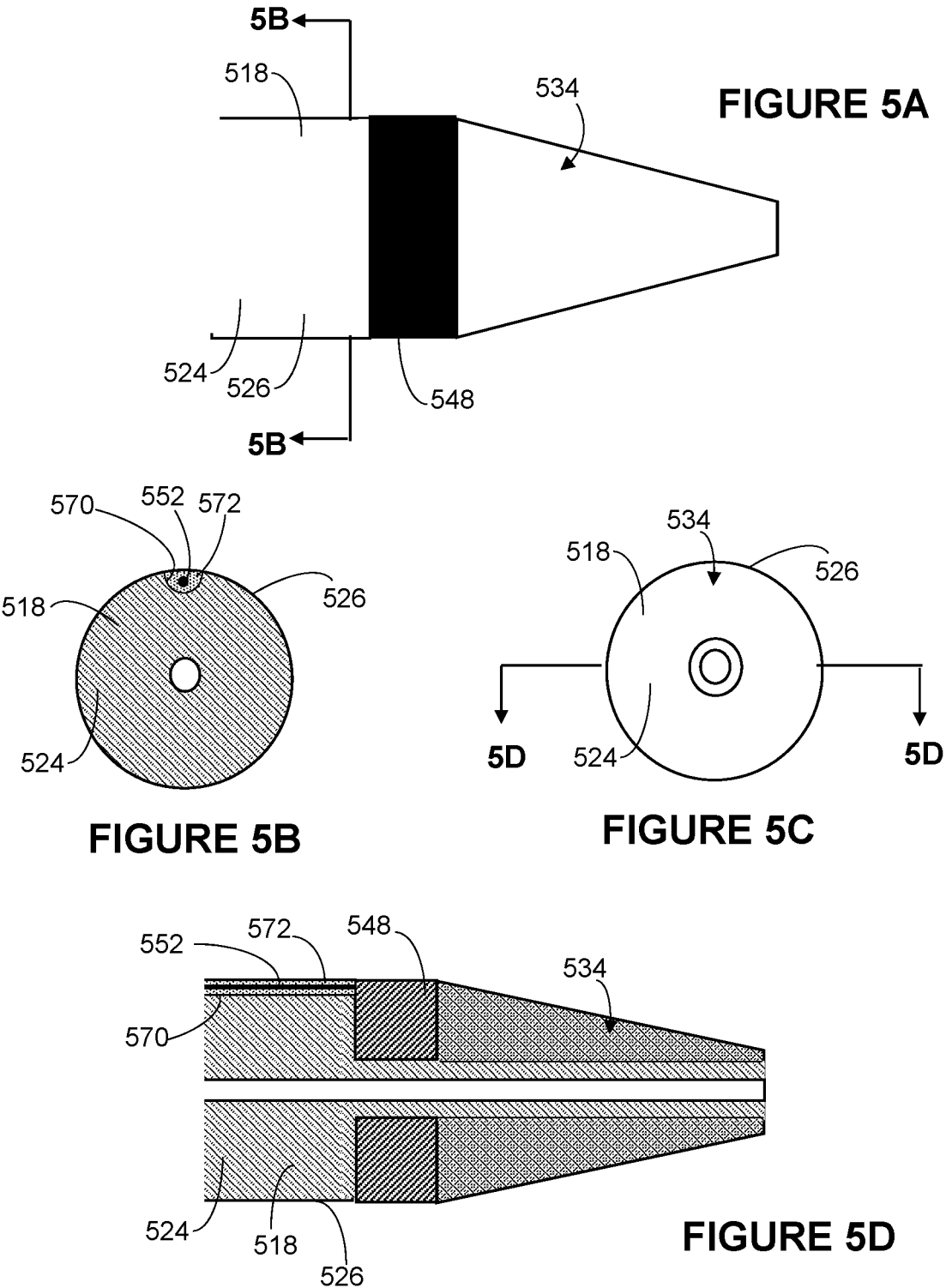
FIG. 5A is an enlarged view of another example dilating tip.
FIG. 5B is a cross-section taken along line 5B-5B in FIG. 5A.
FIG. 5C is an end view of the dilating tip of FIG. 5A.
FIG. 5D is a cross-section taken along line 5D-5D in FIG. 5C.

Referring now to FIGS. 4A to 4C, an alternative example of a dilating tip is shown. In FIG. 4, features that are like those of FIGS. 1 to 3 will be referred to with like reference numerals, incremented by 300. The dilating tip 434 of FIG. 4 is similar to the dilating tip 134 of FIGS. 1 to 3; however, the dilating tip 434 is of a multi-piece construction. Specifically, in the example shown, the dilating tip 434 includes a proximal piece 462, and a distal piece 464. The proximal piece 462 is stepped to define a distal-facing shoulder surface 466, and has a neck 468 extending distally from the shoulder surface 466. The EAM electrode 448 is annular and is received on the neck 468 and abuts the shoulder surface 466. The distal piece 464 is received on the neck 468 distally of the EAM electrode 448 and abuts the EAM electrode 448. The proximal piece 462, EAM electrode 448, and distal piece 464 can be secured together in a variety of ways, such as by adhering and/or friction.

Referring now to FIGS. 5A to 5D, another alternative example of a dilating tip is shown. In FIG. 5, features that are like those of FIGS. 1 to 3 will be referred to with like reference numerals, incremented by 400. The dilating tip 534 of FIG. 5 is similar to the dilating tip 134 of FIGS. 1 to 3; however, the electrical conductor 552 is embedded in the sidewall 524 of the elongate member 518. Specifically, the circumferential outer surface 526 of the elongate member 518 has a longitudinal groove 570 defined therein. The groove 570 extends from the EAM electrode 548 to the proximal end portion (not shown) of the elongate member 518. The electrical conductor 552 is seated in the groove 570, and a strip of material 572 (e.g. plastic or glue) fills the groove 570 over the electrical conductor 552.

Figure 6A:
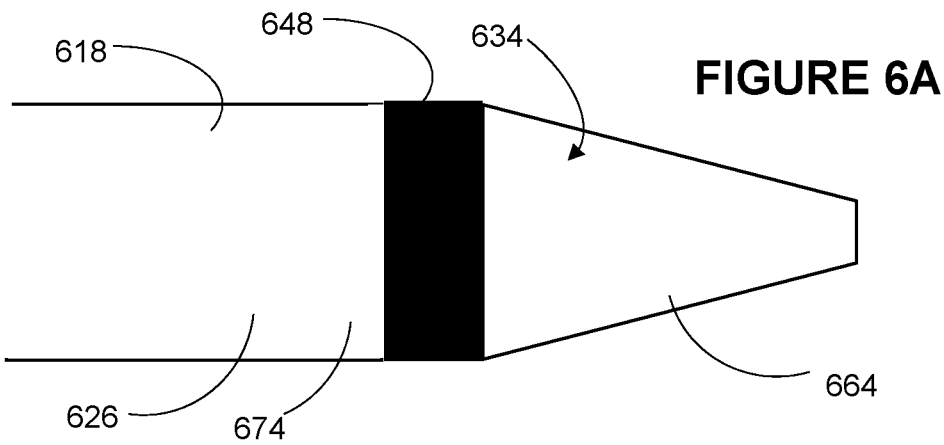
FIG. 6A is an enlarged view of another example dilating tip.
Figure 6B:
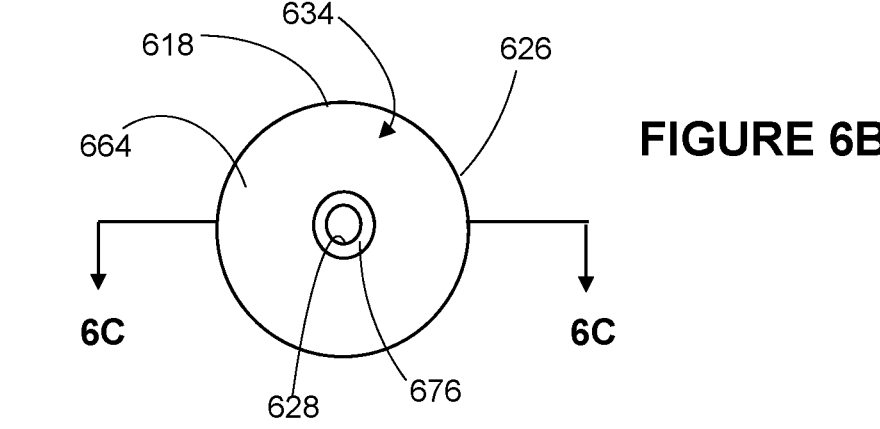
FIG. 6B is an end view of the dilating tip of FIG. 6A.
Figure 6C:
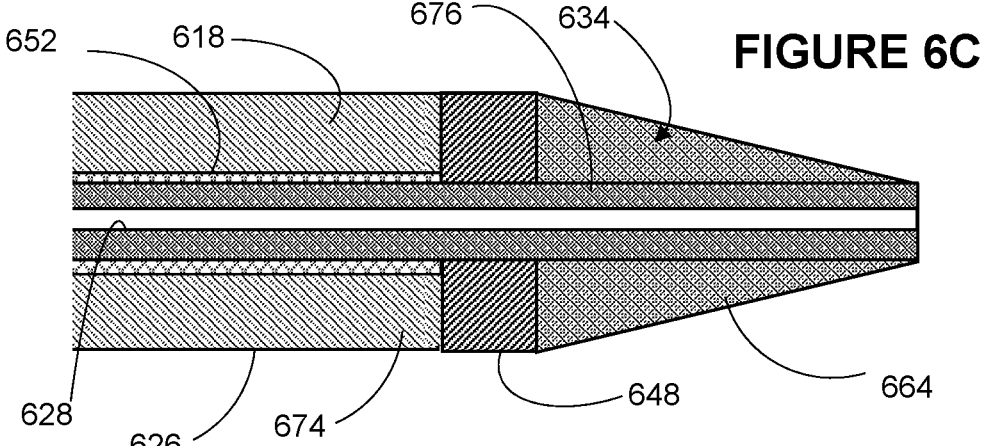
FIG. 6C is a cross-section taken along line 6C-6C in FIG. 6B.

Referring now to FIGS. 6A to 6C, another alternative example of a dilating tip is shown. In FIG. 6, features that are like those of FIGS. 1 to 3 will be referred to with like reference numerals, incremented by 500. The dilating tip 634 of FIG. 6 is similar to the dilator of FIGS. 1 to 3; however, the elongate member 618 includes an outer tube 674, which defines the circumferential outer surface 626, and an inner liner 676 within the outer tube 674, which defines the circumferential inner surface 628. The inner liner 676 can be, for example, a polyimide or polytetrafluoroethylene liner, and the outer tube 674 can be made of a plastic such as HDPE.

In the example of FIG. 6, the electrical conductor 652 is defined by a tubular braid of metallic wires, which is positioned between the outer tube 674 and inner liner 676.

Optionally, in order to fabricate the dilator of FIG. 6, the outer tube 674, electrical conductor 652, EAM electrode 648, and inner liner 676 can first be assembled together, and the EAM electrode 648 can be swaged to form an electrical connection between the EAM electrode 648 and the electrical conductor 652. Then, the material of the outer tube 674 can be re-flowed (e.g. by the application of heat) to join the outer tube 674, electrical conductor 652, and inner liner 676. A distal piece 664 of the dilating tip 634 can then be joined to the assembly. The system end (not shown) of the electrical conductor 652 can then be exposed for connection to the EAM system 104, optionally by skiving.

Figure 7:
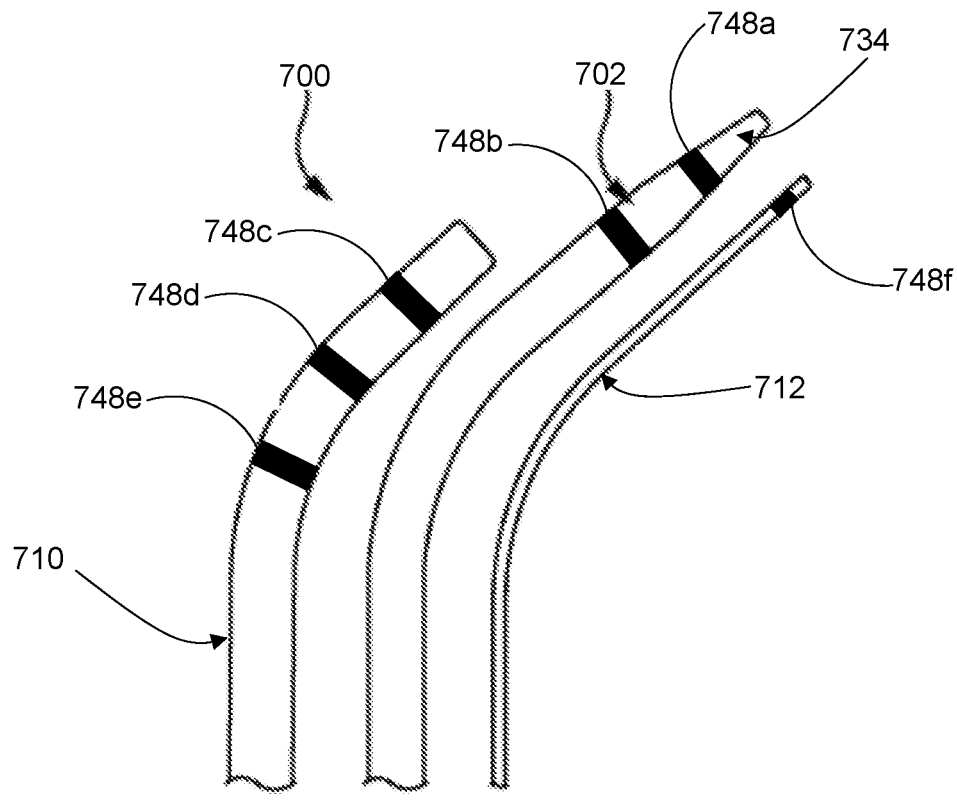
FIG. 7 is a partial perspective view of a sheath, dilator, and perforation device of another example surgical perforation system.

Referring now to FIG. 7, another example of a surgical perforation system is shown. In FIG. 7, features that are like those of FIG. 1 will be referred to with like reference numerals, incremented by 600. In FIG. 7, only the dilator 702, sheath 710, and RF perforation device 712 of the system 700 are shown; the remaining parts of the system 700 can be the same as or similar to the parts shown in FIG. 1. The system 700 of FIG. 7 includes additional EAM electrodes. Specifically, the system 700 includes a first EAM electrode 748a associated with the dilating tip, as described above with respect to FIGS. 1 to 3. Additionally, the system includes a second EAM electrode 748b on the dilator 702 and spaced from the first EAM electrode 748a; third 748c, fourth 748d, and fifth 748e EAM electrodes on the sheath 710; and a sixth EAM electrode 748f on the RF perforation device 712. The second through sixth EAM electrodes (748b-748f) are connectable to the EAM signal generator via additional electrical conductors (not shown). The use of additional EAM electrodes can allow for additional location data to be determined. For example, the location of the sheath 710, or the location dilating tip 734 with respect to the sheath 710, can be determined. Additionally, by providing additional electrodes, the orientation of the sheath or dilator may be determined. For example, providing at least two electrodes on each of the sheath and dilator allows the determination of the direction in which the devices are oriented.

In a further alternative example of a dilator (not shown), the EAM electrode can be removable from the elongate member. For example, the elongate member of the dilator can be a standard dilator (e.g. one known in the art). The EAM electrode, connected to the electrical conductor, can be separate from the elongate member. For example, the EAM electrode can be secured to the perforation device. The EAM electrode can be advanced through the lumen of the elongate member, until the EAM electrode is at the distal end of the dilator. The assembly can be calibrated so that the extent to which the EAM electrode should be advanced to reach the distal end is known.

Referring now to FIGS. 8 to 13, a method for medical dilation, specifically for creation and dilation of a transseptal perforation, will be described. As will be described in more detail, at various points during the method, the EAM electrode and EAM system can be engaged to determine the location of the dilating tip of the dilator—i.e. EAM signals can be received from the EAM electrode of the dilator, and based on the EAM signals, the location of the dilating tip of the dilator can be determined, and optionally mapped and tracked. This can enhance safety of the procedure. The method will be described with reference to the system 100 and dilator 102 as shown in FIGS. 1 to 3; however, the method is not limited to being carried out with system 100 and dilator 102, and the system 100 and dilator 102 are not limited to use according to the described method.

Figures 8, 9:
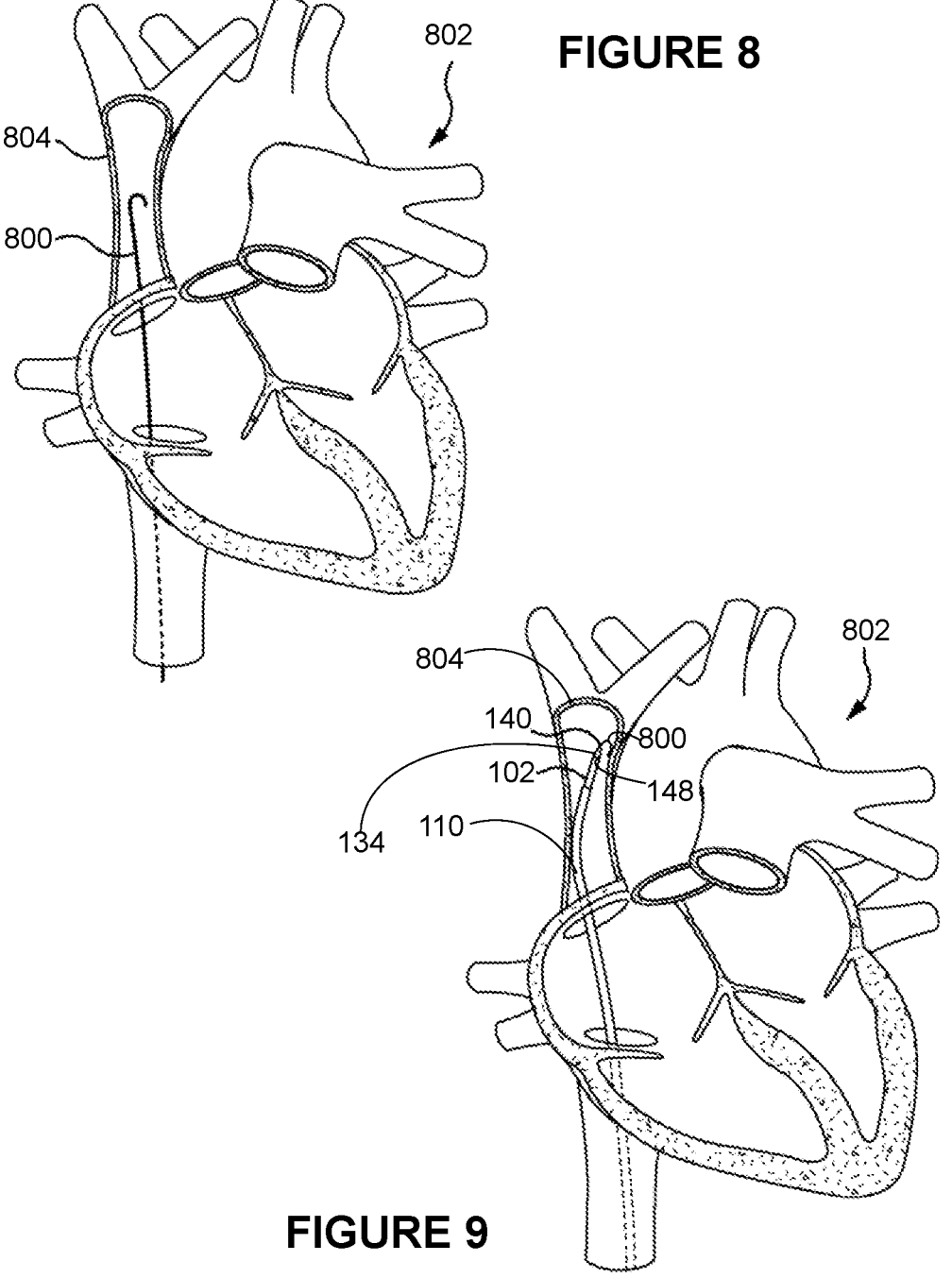
FIG. 8 is a schematic view showing a first step of an example method for creation and dilation of a transseptal perforation.
FIG. 9 is a schematic view showing a second step of the example method for creation and dilation of a transseptal perforation of FIG. 8.

Referring to FIG. 8, a guidewire 800 can be advanced via the femoral vein towards the heart 802, and "parked" in the superior vena cava (SVC) 804.

Referring to FIG. 9, with the dilator 102 in the sheath 110, and with the dilating tip 134 extending proud of the sheath 110, the dilator 102 and sheath 110 can be advanced over the guidewire 800 towards the SVC 804. The guidewire 800 can then be removed, and the RF perforation device 112 (not shown in FIG. 9) can be advanced through the dilator 102 until the perforation electrode 113 (not shown in FIG. 9) of the RF perforation device 112 is just shy of the distal end 140 of the dilator 102.

As mentioned above, in addition to the EAM electrode 148 of the dilator 102 being connected to the EAM system 104 (not shown in FIGS. 8 to 13), the perforation electrode 113 of the RF perforation device 112 can be connected to the EAM system 104 and can serve as an additional EAM electrode. After the RF perforation device 112 has been advanced through the dilator 102 and the perforation electrode 113 is exposed from the dilator 102 or the distal tip of the perforation device 112 is flush with the distal tip of the dilator 102, the positioning of the perforation device 112 can be confirmed using the EAM system 104. Specifically, the EAM system 104 can be engaged, and based on the EAM signal received from the EAM electrode 148 and the perforation electrode 113, the location of the perforation electrode 113 with respect to the dilating tip 134 can be determined. For example, if the EAM system shows that the perforation electrode 113 is proud of the dilating tip 134, it can be determined that the perforation electrode 113 has been advanced too far into the dilator 102. Alternatively, if the perforation electrode 113 cannot be detected by the EAM system, it can be concluded that the perforation electrode 113 is shrouded within the dilating tip 134, and therefore correctly positioned. Additionally, by providing both a perforation electrode 113 and an EAM electrode 148, the relative positioning between the two may be mapped to allow determination of the orientation of the combined assembly.

In some examples, the system 100 can further be configured to provide an alert if the perforation electrode 113 advances distal of the distal end 140 of the dilator 102.

Optionally, at this point, if anatomical data is desired, the user can refer to CT or MRI data.

Referring now to FIG. 10, with the EAM electrode 148 and EAM system 104 engaged to track the location of the dilating tip 134 and the perforation electrode 113 (not shown in FIG. 10), the sheath 110, dilator 102, and perforation device 112 can be advanced towards a target anatomical location to position the dilating tip 134 at the target location. The target anatomical location can be, for example, the fossa ovalis 806 of the atrial septum 808. The EAM electrode 148 and EAM system 104 can be used to confirm the positioning of the dilating tip 134 against the fossa ovalis 806, and also to confirm that the perforation electrode 113 is flush with the distal end 140 of the dilator 102.

Referring to FIG. 11, the perforation device 112 can then be engaged and advanced out of the dilator 102, to create a perforation in the atrial septum 808.

Referring to FIG. 12, the dilating tip 134 can then be advanced through the perforation, to dilate the perforation. Specifically, the dilating tip 134, together with the EAM electrode 148, can be advanced through the perforation. Prior to, during and/or after advancement of the dilating tip 134 and EAM electrode 148, the EAM electrode 148 and EAM system 104 can be engaged to determine the location of the dilating tip 134. This can help to ensure that the perforation is sufficiently dilated, while also helping to ensure that the dilating tip 134 does not contact and thereby damage non-target tissues (e.g. the location of the dilating tip with respect to the left atrial wall can be visualized).

Following dilation of the perforation, various procedures can be carried out. At the desired time, as shown in FIG. 13, the dilator 102 and sheath 110 can be withdrawn from the heart 802. Optionally, during withdrawal, the EAM electrode 148 and EAM system 104 can be engaged, to determine the location of the dilating tip 134.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A medical dilator, comprising:
   an elongate member having a proximal end portion, an opposed distal end portion, and a lumen extending through the elongate member from the proximal end portion to the distal end portion;
   a dilating tip at the distal end portion, the dilating tip having a first end of enlarged cross-sectional area and tapering going in the distal direction to a second end of reduced cross-sectional area;
   a first electrode associated with the dilating tip;
   the dilating tip including a proximal piece having a distal-facing shoulder surface and a neck extending distally from the shoulder surface;
   the dilating tip further including a distal piece received on the neck distal to and abutting the first electrode;
   the first electrode having an annular shape and being positioned on the neck and abutting the distal-facing shoulder surface; and
   an electrical conductor electrically connected to the first electrode and extending proximally from the first electrode towards the proximal end portion for electrical connection with an electroanatomical mapping system.

2. The medical dilator of claim 1, wherein the first electrode has an electrode outer surface, and the first electrode outer surface is flush with a dilating tip circumferential outer surface.

3. The medical dilator of claim 1, wherein the dilating tip has a tip circumferential outer surface, a tip circumferential inner surface, and a tip sidewall extending between the tip circumferential inner surface and the tip circumferential outer surface, and the electrical conductor extends from the first electrode through the tip sidewall and into the lumen.

4. The medical dilator of claim 1, wherein the elongate member has a circumferential outer surface, a circumferential inner surface, and a sidewall extending along the length of the elongate member between the circumferential inner surface and the circumferential outer surface, and the electrical conductor is embedded in the sidewall and extends from the first electrode to the proximal end portion.

5. The medical dilator of claim 4, wherein the circumferential outer surface has a longitudinal groove defined therein and extending from the first electrode to the proximal end portion, and wherein the electrical conductor is seated in the longitudinal groove.

6. The medical dilator of claim 4, wherein the elongate member comprises an outer tube defining the circumferential outer surface, and an inner liner within the outer tube and defining the circumferential inner surface, and wherein the electrical conductor is positioned between the outer tube and the inner liner.

7. The medical dilator of claim 6, wherein the electrical conductor is a tubular braid.

8. The medical dilator of claim 1, wherein the first electrode is removable from the elongate member.

9. The medical dilator of claim 1, further comprising a second electrode mounted to the elongate member and spaced from the first electrode.

10. The medical dilator of claim 1, wherein the first electrode is radiopaque.

11. The medical dilator of claim 10, wherein the first electrode comprises platinum-iridium.

12. The medical dilator of claim 1, wherein the first electrode has an echogenic profile.

13. The medical dilator of claim 12, wherein the first electrode comprises a coil.

14. A kit of parts for medical perforation system, the kit of parts comprising:
a medical dilator comprising an elongate member having a proximal end portion, an opposed distal end portion, and a lumen extending through the elongate member from the proximal end portion to the distal end portion; a dilating tip at the distal end portion, the dilating tip having first end of enlarged cross-sectional area and tapering going in the distal direction to a second end of reduced cross-sectional area; the dilating tip including a proximal piece having a distal-facing shoulder surface and a neck extending distally from the shoulder surface; the dilating tip further including a distal piece received on the neck; at least a first electrode associated with the dilating tip, the first electrode having an annular shape and being positioned on the neck and abutting the distal-facing shoulder surface; an electrical conductor electrically connected to the first electrode and extending proximally from the first electrode to the proximal end portion for electrical connection with an electroanatomical mapping system, wherein the electrical conductor is electrically insulated between the first electrode and the electroanatomical mapping system;
a sheath for receiving the medical dilator; and
a perforation device receivable in the lumen.

15. The kit of parts of claim 14, further comprising at least a second electrode, the second electrode secured to the sheath.

16. The kit of parts of claim 14, further comprising at least a second electrode, the second electrode secured to the elongate member.

17. The kit of parts of claim 14, further comprising at least a second electrode, the second electrode secured to the perforation device.

18. A medical dilation system, comprising:
a medical dilator comprising an elongate member having a proximal end portion, an opposed distal end portion, and a lumen extending through the elongate member from the proximal end portion to the distal end portion; a dilating tip at the distal end portion, the dilating tip having first end of enlarged cross-sectional area and tapering going in the distal direction to a second end of reduced cross-sectional area; the dilating tip including a proximal piece having a distal-facing shoulder surface and a neck extending distally from the shoulder surface; the dilating tip further including a distal piece received on the neck; at least a first electrode associated with the dilating tip, the first electrode having an annular shape and being positioned on the neck and abutting the distal-facing shoulder surface;
and an electrical conductor electrically connected to the first electrode and extending proximally from the first electrode to the proximal end portion; and
an electroanatomical mapping system electrically connectable to the electrical conductor and configured to receive an electroanatomical mapping signal from the first electrode and determine a location of the dilating tip based on the electroanatomical mapping signal.

* * * * *